United States Patent
Le

(10) Patent No.: US 9,655,606 B2
(45) Date of Patent: May 23, 2017

(54) LARGE BORE INTRODUCER WITH IMPROVED SEAL

(71) Applicant: St. Jude Medical Puerto Rico LLC, Caguas, PR (US)

(72) Inventor: Khoi Le, Excelsior, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 274 days.

(21) Appl. No.: 13/772,747

(22) Filed: Feb. 21, 2013

(65) Prior Publication Data

US 2014/0039263 A1 Feb. 6, 2014

Related U.S. Application Data

(60) Provisional application No. 61/679,504, filed on Aug. 3, 2012.

(51) Int. Cl.
| | |
|---|---|
| A61B 1/32 | (2006.01) |
| A61B 17/02 | (2006.01) |
| B23P 19/04 | (2006.01) |
| A61B 17/34 | (2006.01) |
| A61M 39/06 | (2006.01) |

(52) U.S. Cl.
CPC ...... *A61B 17/0218* (2013.01); *A61B 17/3462* (2013.01); *A61M 39/0613* (2013.01); *B23P 19/047* (2013.01); *A61M 2039/064* (2013.01); *Y10T 29/49863* (2015.01)

(58) Field of Classification Search
CPC ............ A61B 17/3423; A61B 17/3462; A61B 2017/3464; A61B 2017/3466; A61B 17/0218; A61B 2017/0225

USPC ............ 600/201, 205, 206, 204; 604/167.01, 604/167.03, 167.04
See application file for complete search history.

(56) References Cited

U.S. PATENT DOCUMENTS

| | | |
|---|---|---|
| 3,470,875 A | 10/1969 | Johnson |
| 5,000,745 A | 3/1991 | Guest et al. |
| 5,431,666 A | 7/1995 | Sauer et al. |
| 5,520,655 A | 5/1996 | Davila et al. |
| (Continued) | | |

FOREIGN PATENT DOCUMENTS

| | | |
|---|---|---|
| EP | 0399769 A1 | 11/1990 |
| EP | 0771574 A1 | 5/1997 |
| (Continued) | | |

OTHER PUBLICATIONS

PCT Communication Relating to the Results of the Partial International Search for International Application No. PCT/US2012/041196, mailed Sep. 11, 2012.

(Continued)

*Primary Examiner* — Ellen C Hammond
*Assistant Examiner* — Christina Negrellirodrigue
(74) *Attorney, Agent, or Firm* — Holland & Hart

(57) ABSTRACT

An introducer includes a housing and a flexible seal. The housing includes a hub, a cap, and a lumen. The flexible seal is positioned across the lumen and retained between the hub and the cap. The seal includes a top surface and a bottom surface, a bottom slit formed in the bottom surface, and a top slit formed in the top surface. The top slit crosses the bottom slit. The seal member is biased by an interface between the hub and the cap to at least partially close the top slit and at least partially open the bottom slit.

23 Claims, 12 Drawing Sheets

(56) References Cited

U.S. PATENT DOCUMENTS

| | | | |
|---|---|---|---|
| 5,520,702 A | 5/1996 | Sauer et al. |
| 5,562,686 A | 10/1996 | Sauer et al. |
| 5,613,974 A | 3/1997 | Andreas et al. |
| 5,643,292 A | 7/1997 | Hart |
| 5,674,231 A | 10/1997 | Green et al. |
| 5,700,273 A | 12/1997 | Buelna et al. |
| 5,709,692 A | 1/1998 | Mollenauer et al. |
| 5,728,114 A | 3/1998 | Evans et al. |
| 5,766,183 A | 6/1998 | Sauer |
| 5,807,350 A | 9/1998 | Diaz |
| 5,860,990 A | 1/1999 | Nobles et al. |
| 5,972,005 A | 10/1999 | Stalker et al. |
| 6,036,699 A | 3/2000 | Andreas et al. |
| 6,048,357 A | 4/2000 | Kontos |
| 6,059,800 A | 5/2000 | Hart et al. |
| 6,136,010 A | 10/2000 | Modesitt et al. |
| 6,355,050 B1 | 3/2002 | Andreas et al. |
| 6,416,499 B2 | 7/2002 | Paul, Jr. |
| 6,562,052 B2 | 5/2003 | Nobles et al. |
| 6,623,509 B2 | 9/2003 | Ginn |
| 6,641,592 B1 | 11/2003 | Sauer et al. |
| 6,896,692 B2 | 5/2005 | Ginn et al. |
| 6,911,034 B2 | 6/2005 | Nobles et al. |
| 6,932,824 B1 | 8/2005 | Roop et al. |
| 6,964,668 B2 | 11/2005 | Modesitt et al. |
| 6,969,397 B2 | 11/2005 | Ginn |
| 7,001,400 B1 | 2/2006 | Modesitt et al. |
| 7,083,635 B2 | 8/2006 | Ginn |
| 7,235,087 B2 | 6/2007 | Modesitt et al. |
| 7,361,183 B2 | 4/2008 | Ginn |
| 7,390,328 B2 | 6/2008 | Modesitt |
| 7,553,319 B2 | 6/2009 | Bagaoisan et al. |
| 7,601,161 B1 | 10/2009 | Nobles et al. |
| 7,621,937 B2 | 11/2009 | Pipenhagen et al. |
| 7,686,821 B2 | 3/2010 | Hathaway et al. |
| 7,731,726 B2 | 6/2010 | Belhe et al. |
| 7,744,610 B2 | 6/2010 | Hausen |
| 7,752,853 B2 | 7/2010 | Singh et al. |
| 7,753,933 B2 | 7/2010 | Ginn et al. |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,985,240 B2 | 7/2011 | Bagaoisan et al. |
| 8,029,476 B2 | 10/2011 | Rosenberg et al. |
| 8,048,092 B2 | 11/2011 | Modesitt et al. |
| 8,083,768 B2 | 12/2011 | Ginn et al. |
| 8,192,456 B2 | 6/2012 | Holman et al. |
| 2005/0085854 A1 | 4/2005 | Ginn |
| 2005/0148823 A1* | 7/2005 | Vaugh ............... A61B 17/0293 600/206 |
| 2005/0192537 A1* | 9/2005 | Osborne ........... A61M 39/0606 604/167.01 |
| 2006/0212071 A1 | 9/2006 | Ginn et al. |
| 2008/0065151 A1 | 3/2008 | Ginn |
| 2009/0099578 A1 | 4/2009 | Heneveld et al. |
| 2009/0306685 A1 | 12/2009 | Fill |
| 2010/0042118 A1 | 2/2010 | Garrison et al. |
| 2010/0305408 A1* | 12/2010 | Albrecht ............... A61B 17/02 600/208 |
| 2011/0071567 A1 | 3/2011 | Modesitt et al. |

FOREIGN PATENT DOCUMENTS

| | | |
|---|---|---|
| EP | 0818178 A2 | 1/1998 |
| EP | 1158907 A1 | 12/2001 |
| EP | 1327419 A2 | 7/2003 |
| EP | 1349501 A2 | 10/2003 |
| EP | 1677682 A2 | 7/2006 |
| EP | 1972282 A2 | 9/2008 |
| EP | 2147640 A2 | 1/2010 |
| EP | 2298180 A1 | 3/2011 |
| WO | 9703613 A1 | 2/1997 |
| WO | 0051498 | 9/2000 |
| WO | 0078226 A1 | 12/2000 |
| WO | 2010081106 A1 | 7/2010 |
| WO | 2011115048 A1 | 9/2011 |

OTHER PUBLICATIONS

Notification of Transmittal of the International Search Report and the Written Opinion of the International Searching Authority, or the Declaration for International Application No. PCT/US2013/027070, mailed May 21, 2013, (12 pages).

Notification of Transmittal of the International Search Report and the Written Opinion of the International Searching Authority, or the Declaration for International Application No. PCT/US2012/064768, mailed Feb. 19, 2013, (18 pp.).

Notification of Transmittal of the International Search Report and the Written Opinion of the International Searching Authority, or the Declaration for International Application No. PCT/US2012/066012, mailed Feb. 19, 2013, (17 pp.).

Notification of Transmittal of the International Search Report and the Written Opinion of the International Searching Authority, or the Declaration for International Application No. PCT/US2012/064770, mailed Feb. 19, 2013, (16 pp.).

* cited by examiner

LARGE BORE INTRODUCER WITH IMPROVED SEAL

RELATED APPLICATION

This claims the benefit of U.S. Provisional App. No. 61/679,504, filed 3 Aug. 2012, which is hereby incorporated by reference herein in its entirety.

TECHNICAL FIELD

The present disclosure relates generally to accessing tissue punctures, and more particularly, to methods and systems for creating a sealed interface between an introducer and a device delivered through the introducer.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an introducer (also referred to as an introducer sheath and an insertion sheath) may be placed in the artery and thereafter instruments (e.g., catheters) may pass through the introducer to an operative position within the artery.

The introducer is typically designed to penetrate the skin and wall of the blood vessel and be positioned within the blood vessel so that surgical implements and medical devices may be advanced and withdrawn through the introducer. In this way, even when multiple surgical implements and medical devices are used in a single procedure, there is a single placement of the introducer through the skin and vessel wall.

Introducers typically include valves that prevent back flow of blood through the introducer while permitting advancement of the surgical implements and medical devices to the vessel. Introducer valves are typically categorized as passive or active. A passive valve generally relies on the deformation of a resilient sealing member by the implement or medical device that is inserted through the valve to form the desired fluid-tight seal. An active valve typically includes a mechanism that moves a sealing member into contact with the implement or medical device.

Whether active or passive, valves generally suffer from a common disadvantage of failing to provide an effective hemostatic seal with a wide range of sizes of implements and medical devices that are advanced through the valve. Passive valves tend to impose substantial friction forces on at least some types of implements and medical devices (e.g., larger devices), thereby making it difficult for the user to insert and withdraw the implement or medical device relative to the introducer. Moving parts in an active valve have greater potential for failure.

The complexity of common endovascular surgical procedures has placed heightened demands on the ability of the introducer to provide a seal with a variety of implements and medical devices. It is common to have a range in size for such implements and medical devices from various small guidewires (0.01 inch diameter) to relatively large dilators and other implements (e.g., 5 French (F) to 20 F).

Opportunities exist for improving such sealing members, especially in large bore introducers (e.g., 18 F) through which different sized and shaped devices are delivered into a patient.

SUMMARY

One aspect of the present disclosure relates to an introducer that includes a housing and a flexible seal. The housing includes a hub, a cap, and a lumen. The flexible seal is positioned across the lumen and retained between the hub and the cap. The flexible seal includes a top surface and a bottom surface, a bottom slit formed in the bottom surface, and a top slit formed in the top surface. The top slit crosses or overlaps the bottom slit. The flexible seal is biased by an interface between the hub and the cap to at least partially close the top slit and at least partially open the bottom slit.

At least one of the first and second slits may have a contoured shape when opened. The bottom slit may be arranged perpendicular to the top slit. The top and bottom slits may each have a depth less than one half of a thickness of the flexible seal. The hub may include a protrusion that biases the flexible seal proximally. The flexible seal may comprise silicone. The flexible seal may include an integral, single-piece construction. The hub and cap may be positioned at a proximal end of the housing. The top slit may be biased completely closed.

Another aspect of the present disclosure relates to a seal member for use in an introducer. The seal member includes a first surface having a first slit that extends through a first partial thickness of the seal member. The seal member also includes a second surface opposed to the first surface and having a second slit. The second slit extends through a second partial thickness of the seal member. The first and second slits are oriented substantially perpendicular to each other.

The first and second slits may overlap. The first and second partial thicknesses may be no greater than 50% of the thickness of the seal member. The seal member may be circular shaped. A continuous portion of the seal member thickness may extend between the first and second slits at a location where the first and second slits overlap.

A further aspect of the present disclosure relates to a method of assembling an introducer. The method includes providing a hub, a cap, and a seal member, wherein the seal member has first and second slits formed in opposing top and bottom surfaces thereof, and the first and second slits extend through a partial thickness of the seal member. The method also includes compressing the seal member between the hub and the cap to at least partially open the bottom slit and at least partially close the top slit.

At least one of the hub and the cap may include a protrusion that biases the seal member proximally when compressing the seal member. The first and second slits may extend through no more than one half of the thickness of the seal member. The introducer may include a lumen, and the seal member extends across the lumen to seal the lumen.

Another example method relates to accessing a body cavity. The method includes providing an introducer, a guidewire, and a dilator. The introducer has a lumen and a seal member extending across in the lumen. The seal member has a first slit formed in a first surface thereof and a second slit formed in second surface thereof. The first and second slits extend through a partial thickness of the sealing member. The method includes inserting the introducer through a tissue puncture and into the cavity, and inserting one of the guidewire and the dilator through the lumen and the first and second slits of the seal member and into the cavity. The seal member provides a seal around a peripheral surface of the guidewire or dilator.

Inserting the guidewire or dilator may tear through the seal member to pass from the bottom slit to the top slit. The introducer may include a hub and a cap, and the seal member is compressed between the hub and cap to at least partially close the first slit and at least partially open the second slit.

The foregoing and other features, utilities, and advantages of the invention will be apparent from the following detailed description with reference to the accompanying drawings.

BRIEF DESCRIPTION OF THE DRAWINGS

The accompanying drawings illustrate various embodiments of the present disclosure and are a part of the specification. The illustrated embodiments are merely examples and do not limit the scope of the invention.

FIG. 11A is a close-up view of the sealing member of FIG. 11.

FIG. 11B is a close-up view of another example sealing member arrangement in accordance with the present disclosure.

Throughout the drawings, identical reference numbers designate similar, but not necessarily identical, elements.

DETAILED DESCRIPTION

Figure 1:
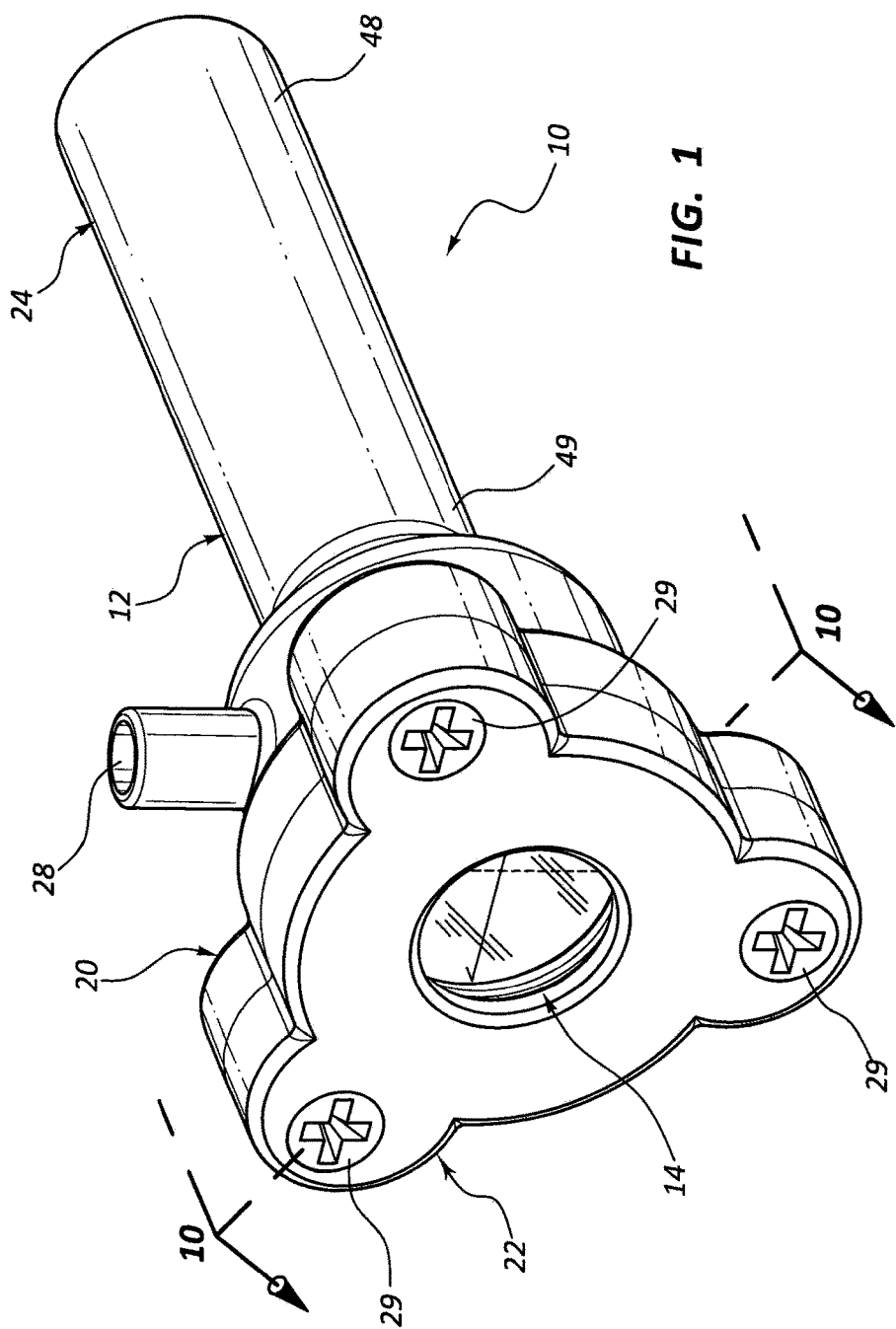
FIG. 1 is a perspective view of an example introducer in accordance with the present disclosure
Figure 2:
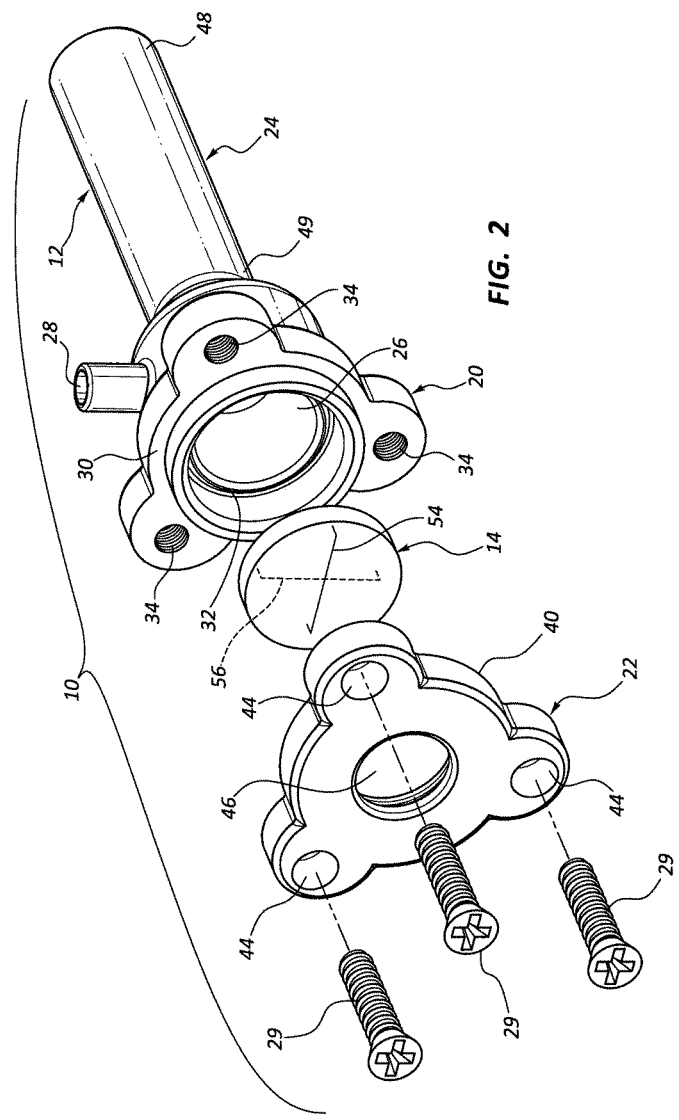
FIG. 2 is an exploded perspective view of the introducer of FIG. 1.
Figure 3:
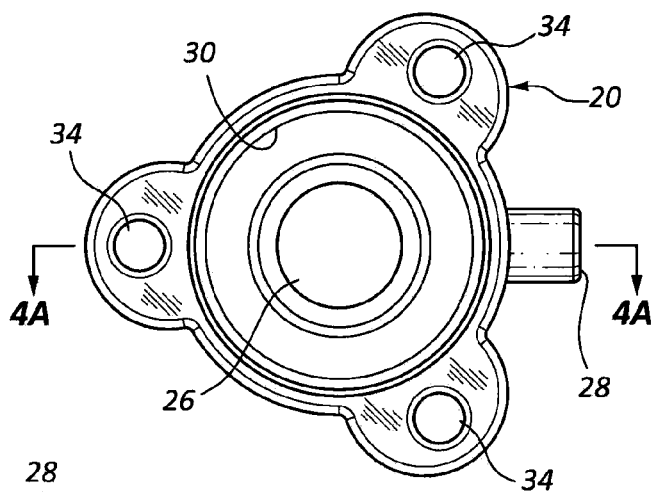
FIG. 3 is an end view of a hub of the introducer of FIG. 1.

The apparatuses and methods disclosed herein may be used to access percutaneous punctures made through a body layer of a patient to gain access to a body cavity. Access through a percutaneous puncture allows a physician to carry out various procedures in or through the body cavity for examination, surgery, treatment and the like. While not meant to be limiting, the systems are illustrated being used to access percutaneous punctures in blood vessels in patients for various procedures. It will be appreciated that the apparatuses and methods are applicable to other procedures requiring access to a puncture through body tissue into a cavity including, for example, laparoscopic surgery and other microscopic surgery techniques using a relatively small incision. Applications of access apparatuses and methods including those implementing principles described herein include access of a percutaneous puncture or incision in tissue separating two internal portions of a living body, such as punctures or incisions in blood vessels, ducts or lumens, gall bladders, livers, hearts, etc.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

One aspect of the present disclosure relates to an introducer configured to provide a sealed interface with instruments of different sizes that extend through the introducer. For example, the introducer may provide a sealed interface with an instrument as large as a 20 French dilator, and after removal of the dilator provide a sealed interface with a relatively small guidewire of less than 0.03 inch in diameter. The introducer may include a flexible seal positioned across a lumen that extends through the introducer. The flexible seal may include multiple slits formed therein. The slits may be positioned on opposing primary surfaces of the flexible seal. The slits may extend through only a partial thickness of the flexible seal. The partial thickness may be less than one half of the thickness of the flexible seal. The slits may criss-cross or overlap when viewed from one of the primary surfaces (e.g., a front or rear of the flexible seal). An instrument inserted through the flexible seal may pass through one of the slits, through an unbroken or continuous portion of the flexible seal, and into the second slit. The unbroken, continuous portion of the flexible seal positioned between the first and second slits may be referred to as a slit interface. An intersection or overlap point of the first and second slits as viewed from the front or rear of the flexible seal may also be referred to as the slit interface.

The flexible seal may be captured between a hub and cap of the introducer. At least one of the hub and cap may include a biasing member that biases the flexible seal into a bowed position (e.g., concave or convex). This bowed position may close the slit on one surface of the flexible seal and open the slit on the opposing surface of the flexible seal. The slit that is open may be facing an entrance into the introducer to promote easier insertion of the instrument through the flexible seal. The closed slit may provide enhanced sealing around the perimeter or peripheral surface of the instrument as the instrument passes through the flexible seal. Tightening the cap against the hub may further compress the flexible seal thereby increasing the bowed shape of the sealing member and affecting the opened/closed state of the slits. Releasing the cap away from the hub may permit the sealing member to move to a rest or uncompressed position. The first and second slits may have the same opened/closed position when in the rest position.

Referring now to FIGS. 1-11, an example introducer 10 is shown including a housing assembly 12 and a seal member 14. The housing assembly may include a hub 20, a cap 22, an insertion portion 24, a lumen 26 extending through the hub 20 and insertion portion 24, a port 28, and a plurality of fasteners 29. The housing assembly 12 captures the seal member 14 between the hub 20 and cap 22. The seal member 14 may provide a sealed interface between the introducer and an instrument that is inserted through the seal member 14 and into a cavity (e.g., a vessel) into which the introducer 10 is positioned.

Figure 4A:
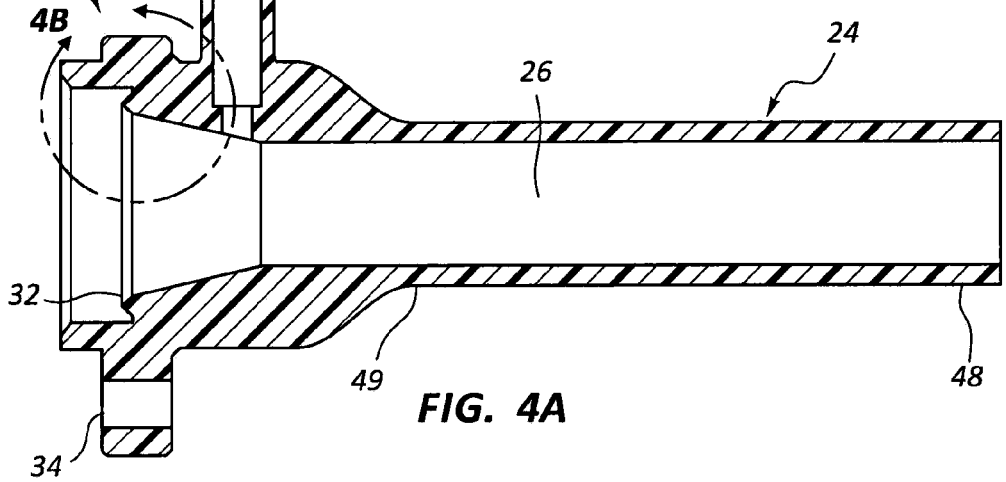
FIG. 4A is a cross-sectional view of the hub of FIG. 3 taken along cross-section indicators 4A-4A.
Figure 4B:
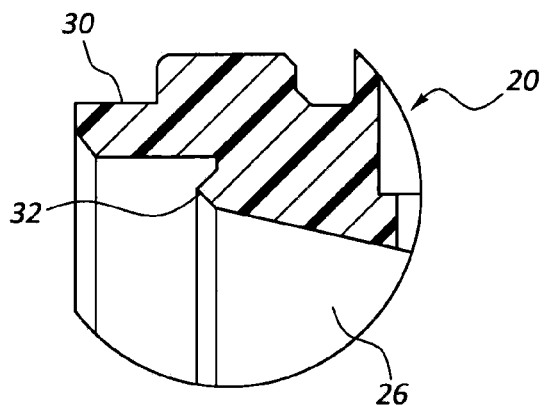
FIG. 4B is a close-up view of the hub of FIG. 4A.
Figure 5:
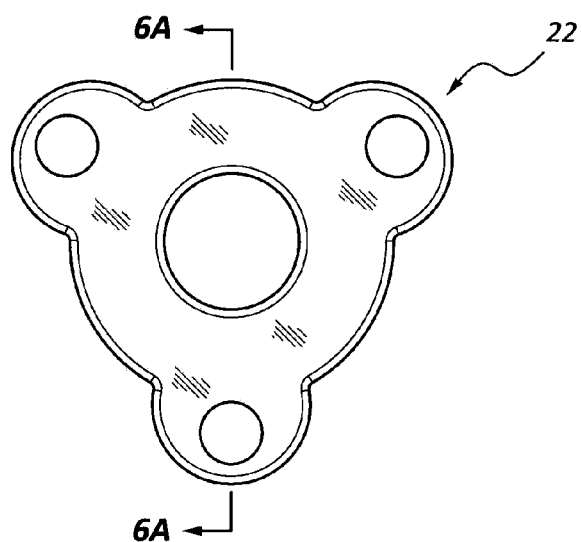
FIG. 5 is an end view of a cap of the introducer of FIG. 1.
Figure 6A:
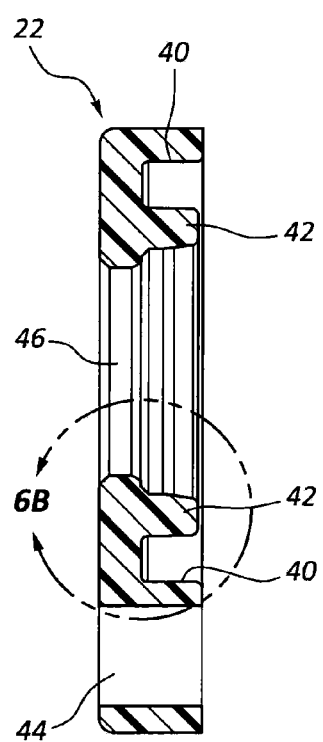
FIG. 6A is a cross-sectional view of the cap of FIG. 5 taken along cross-section indicator 6A-6A.
Figure 6B:
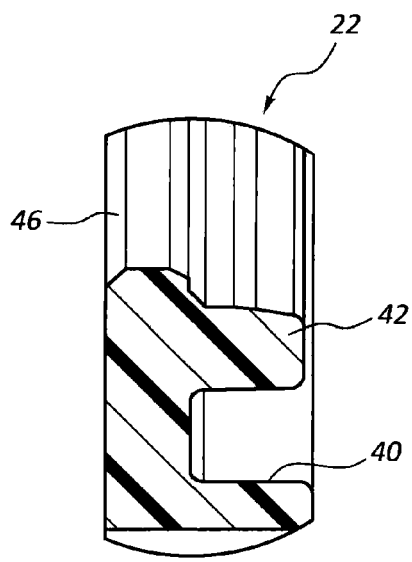
FIG. 6B is a close-up view of the cap of FIG. 6A.

FIGS. 2-4B show the hub 20 having a cap interface 30, a seal biasing member 32, and a plurality of hub fastener bores 34. FIGS. 4A and 4B show the seal biasing member 32 positioned within the hub 20 at a location that contacts a primary surface of the seal member 14 to help capture the seal member between the hub 20 and cap 22. The seal biasing member 32 may have a tapered portion (e.g., pointed portion) that contacts the seal member 14. The seal biasing member 32 may extend continuously around the hub 20. The fasteners 29 extend into the hub fastener bores 34.

Referring to FIGS. 2 and 5-6B, the cap 22 includes a hub interface 40, a seal support 42, a plurality of cap fastener bores 44, and an entrance aperture 46. The seal support 42 is aligned with the seal biasing member 32 as shown in least FIGS. 10 and 11. The seal support 42 may be arranged along a peripheral edge of the seal member 14. In some arrangements, the seal support 42 is positioned radially outward from the seal biasing member 32. The fasteners 29 extend through the cap fastener bores 44 to secure the cap 22 to the hub 20.

Figure 10:
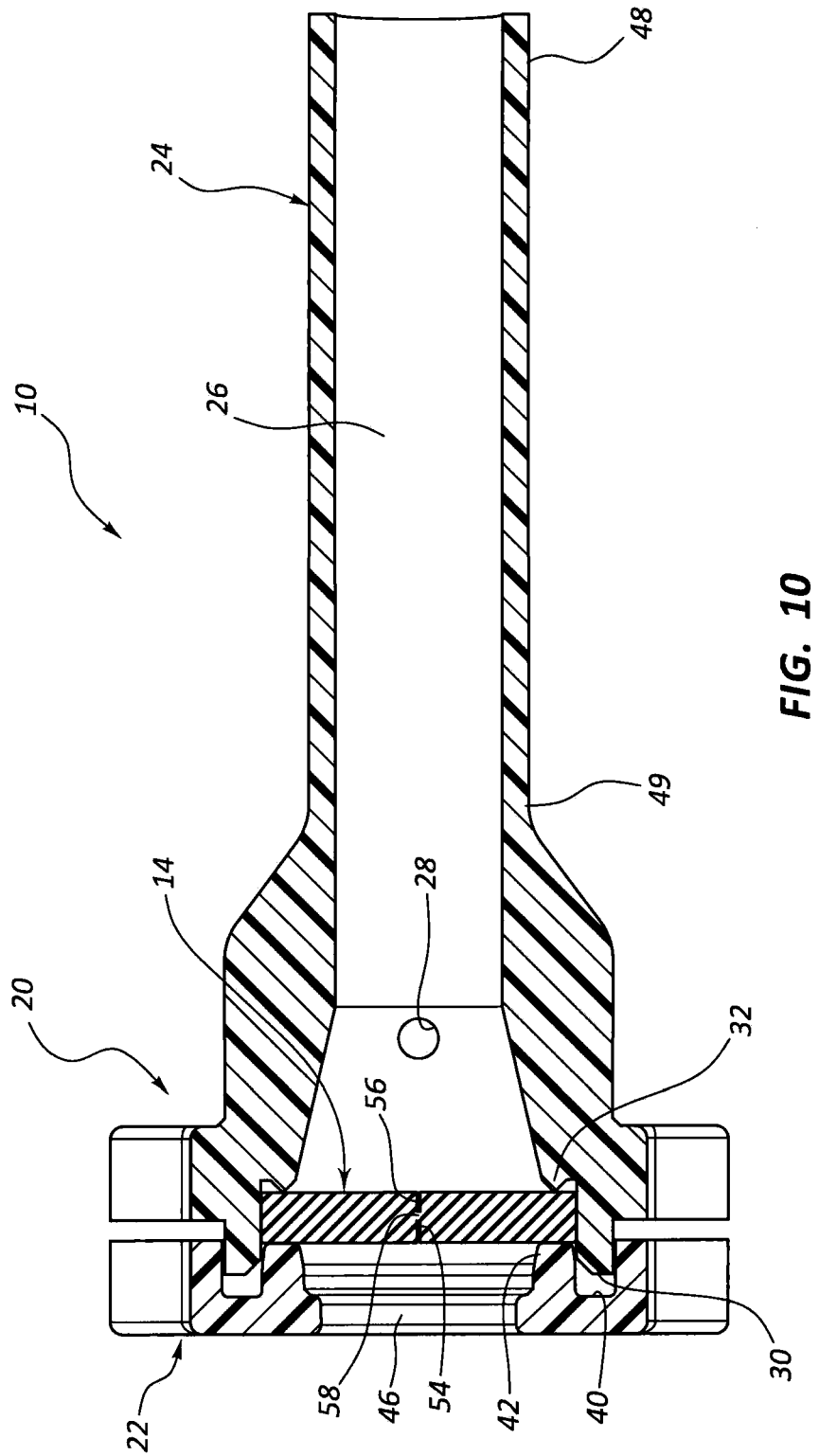
FIG. 10 is a cross-sectional view of the introducer of FIG. 1 with the sealing member in an uncompressed position.
Figure 11:
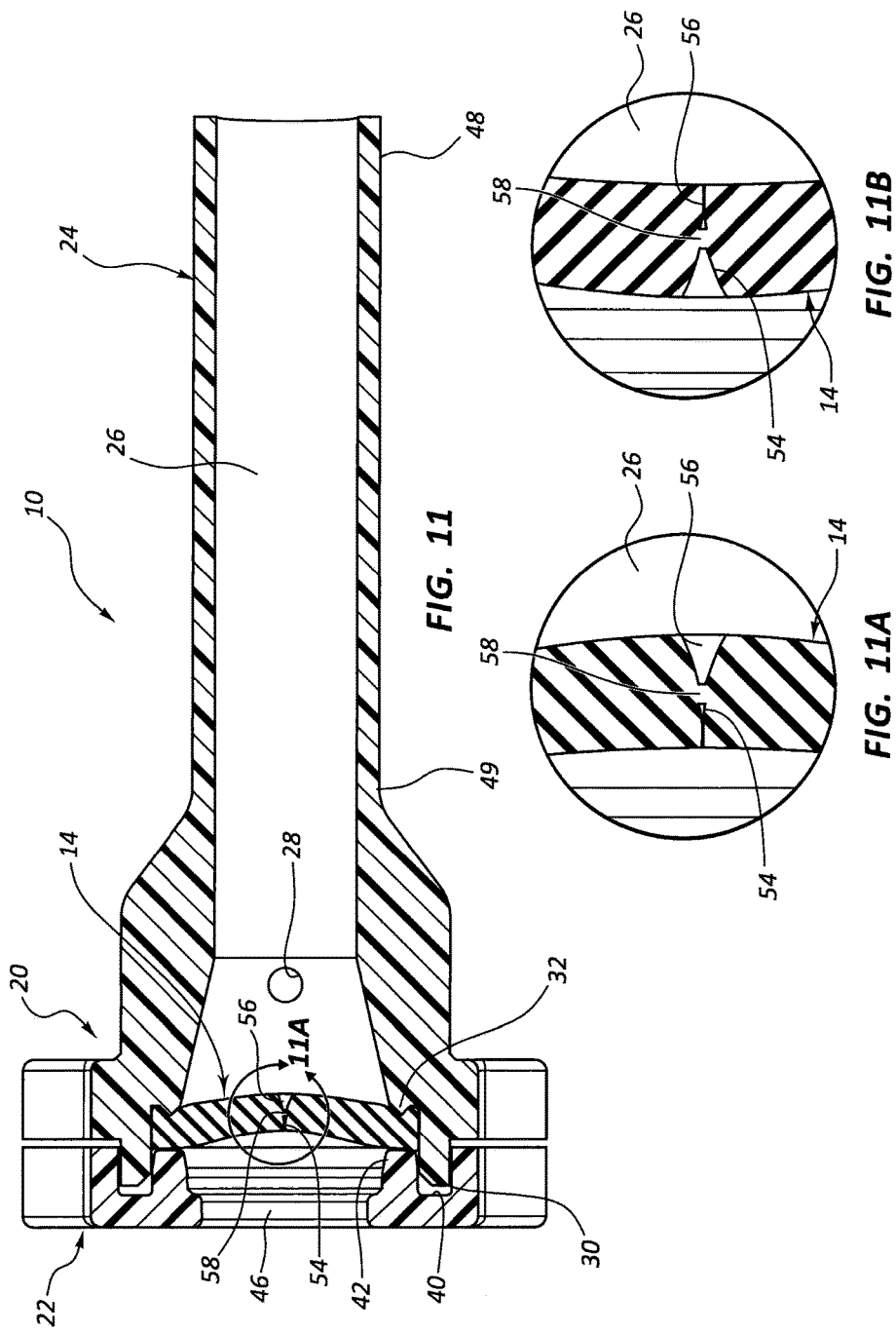
FIG. 11 is a cross-sectional view of the introducer of FIG. 1 with the sealing member in a compressed position.

The seal member 14 may be held in an uncompressed position wherein a first slit 54 (also referred to as a top slit) and a second slit 56 (also referred to as a bottom slit) have the same opened or closed position as shown in FIG. 10. The seal biasing member 32 is positioned radially inward from the circumferential edge of the seal member 14 and the seal support 42. The radially offset position of the seal biasing member 32 may make it possible to apply a biasing force on the seal member 14 that tends to bow a center portion of the seal member 14 away from the entrance aperture 46 of cap 22, as shown in FIGS. 11 and 11A. As the cap 22 is moved towards the hub 20 (e.g., the tighter the cap 22 is secured to the hub 20), additional biasing force is applied by the seal biasing member 32 to the seal member 14. The fasteners 29 may be adjusted to change a position of the cap 22 relative to the hub 20 thereby adjusting the biasing force applied to the seal member 14 by the seal biasing member 32. The biasing force tends to close the first slit 54 and open the second slit 56 as shown in FIG. 11A. Increasing the biasing force further opens the second slit 56 and more tightly closes the first slit 54.

In other arrangements, seal biasing member 32 and seal support 42 may be structured to bow the seal member 14 in an opposite direction as shown in FIG. 11B. Moving the cap 22 further toward the hub 20 in the embodiment of FIG. 11B opens the first slit 54 and closes the second slit 56.

The cap 22 may be connected to the hub 20 using other connecting features in place of the fasteners 29. For example, the cap 22 may be connected to the hub 20 with a threaded interface between the cap 22 and hub 20. Alternatively, other connection methods may be used such as, for example, ultrasonic welding, adhesives, heat welding, or laser welding.

Referring again to FIGS. 2 and 4A, the insertion portion 24 includes distal and proximal ends 48, 49. The distal end 48 is inserted through a tissue layer and vessel wall and into a vessel. Once the distal end 48 is positioned in the vessel, blood tends to backflow into the lumen 26. The seal member 14 stops the blood from flowing out of the introducer 10.

Figure 8:
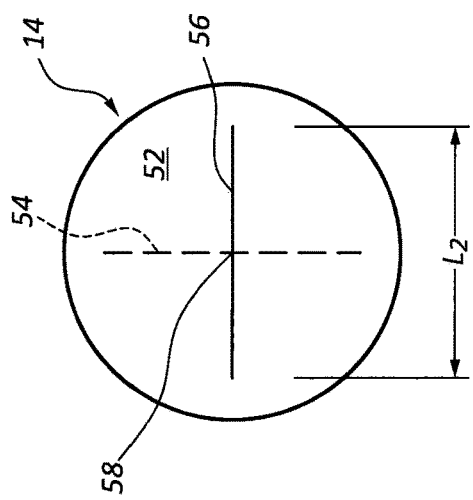
FIG. 8 is a rear view of the sealing member of FIG. 7.
Figure 9:
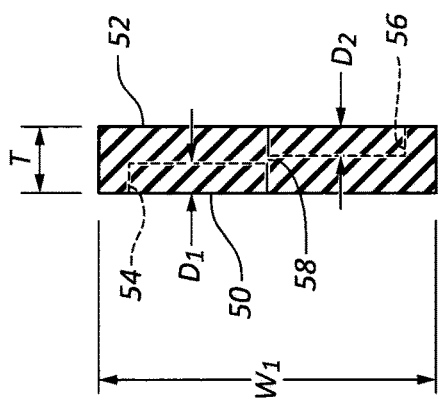
FIG. 9 is a cross-sectional view of the sealing member of FIG. 7 taken along cross-section indicators 9-9.
Figure 7:
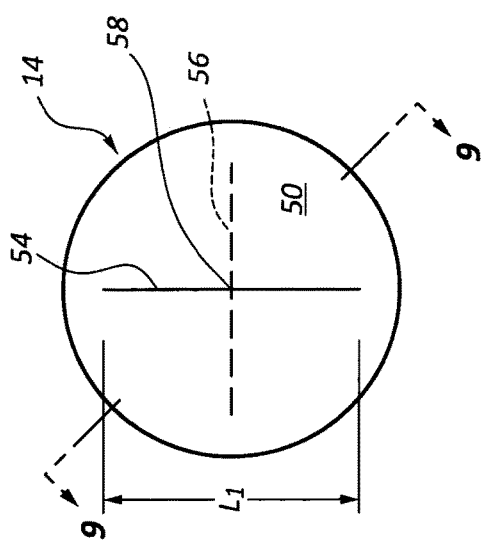
FIG. 7 is a front view of a sealing member of the introducer of FIG. 1.

Referring now to FIGS. 7-9, the seal member 14 includes first and second surfaces 50, 52, first and second slits 54, 56, and a slit interface 58. The slit interface 58 is defined at an intersection or overlap of the first and second slits 54, 56 as shown in FIGS. 7-9. The slit interface 58 may include a portion of unbroken, continuous material of the seal member 14 between the first and second slits 54, 56 as shown in FIG. 9. The slit interface 58 may be arranged at or adjacent to a central axis of the seal member 14.

The first and second slits 54, 56 may include first and second slit depths $D_1$, $D_2$, respectively. The first and second slit depths $D_1$, $D_2$ may each be less than the total thickness T of the seal member 14. In one arrangement, the thickness T is in a range of about 0.01 inches to about 0.1 inches, and more preferably in the range of about 0.05 inches to about 0.08 inches. The first and second slits $D_1$, $D_2$ are typically in the range of about 20% to about 50% of the total thickness T, and more preferably in the range of about 40% to about 45% of the thickness T. In some arrangements, the first and second slits $D_1$, $D_2$ are substantially the same. In other arrangements, one of the first and second slits $D_1$, $D_2$ is greater than the other. In at least one arrangement, the first and second slits $D_1$, $D_2$ is greater than 50% of the total thickness T.

The first and second slits 54, 56 may have lengths $L_1$, $L_2$ respectively. The lengths $L_1$, $L_2$ are typically less the maximum width $W_1$ of the seal member 14. The lengths $L_1$, $L_2$ may be substantially the same. Alternatively, one of the $L_1$, $L_2$ may be greater than the other length.

The seal member may comprise a polymer material such as silicone or other elastic material. In one example, the material of the seal member has a durometer in the range of about 20 A to 30 A.

The seal member may be formed in any desired manner. In at least one example, the seal member is cast into a disk shape. Other forming methods include molding and cutting from a sheet of material. The thickness T of the seal member may vary across the width $W_1$. The variable thickness may provide a contoured shape across at least one of the first and second surfaces 50, 52. The variable thickness may be formed in the seal member 14 using machining techniques such as, for example, milling, or may be formed as part of a molding or casting process.

The first and second slits 54, 56 may be formed in the seal member 14 as part of the formation of the seal member 14 (e.g., as part of the casting or molding process). Alternatively, the first and second slits 54, 56 may be formed by cutting or milling after formation of the seal member 14.

The first and second slits 54, 56 may be arranged generally perpendicular to each other. Other angle orientations may be possible including, for example, orientations in the range of about 30° to about 90°.

As discussed above, the cap 22 may be adjusted relative to hub 20 to provide variable amounts of compression in the seal member 14. Adjusting compression of seal member 14 may adjust the open or closed state of the first and second slits 54, 56. In one example, the cap 22 is adjusted to provide compression of the seal member 14 in a range of about 2% to about 20%, and more preferably in the range of about 2% to 5%. The amount of compression may be optimized for opening and closing the first and second slits 54, 56 based on a number of variables including, for example, the thickness T, the first and second slit depths $D_1$, $D_2$, the slit lengths $L_1$, $L_2$, and the width $W_1$ of the seal member 14. Other variables may include the type of material and its durometer, whether the seal member has a variable thickness, and the structure and location of the seal biasing member 32 and seal support 42.

Figure 12:
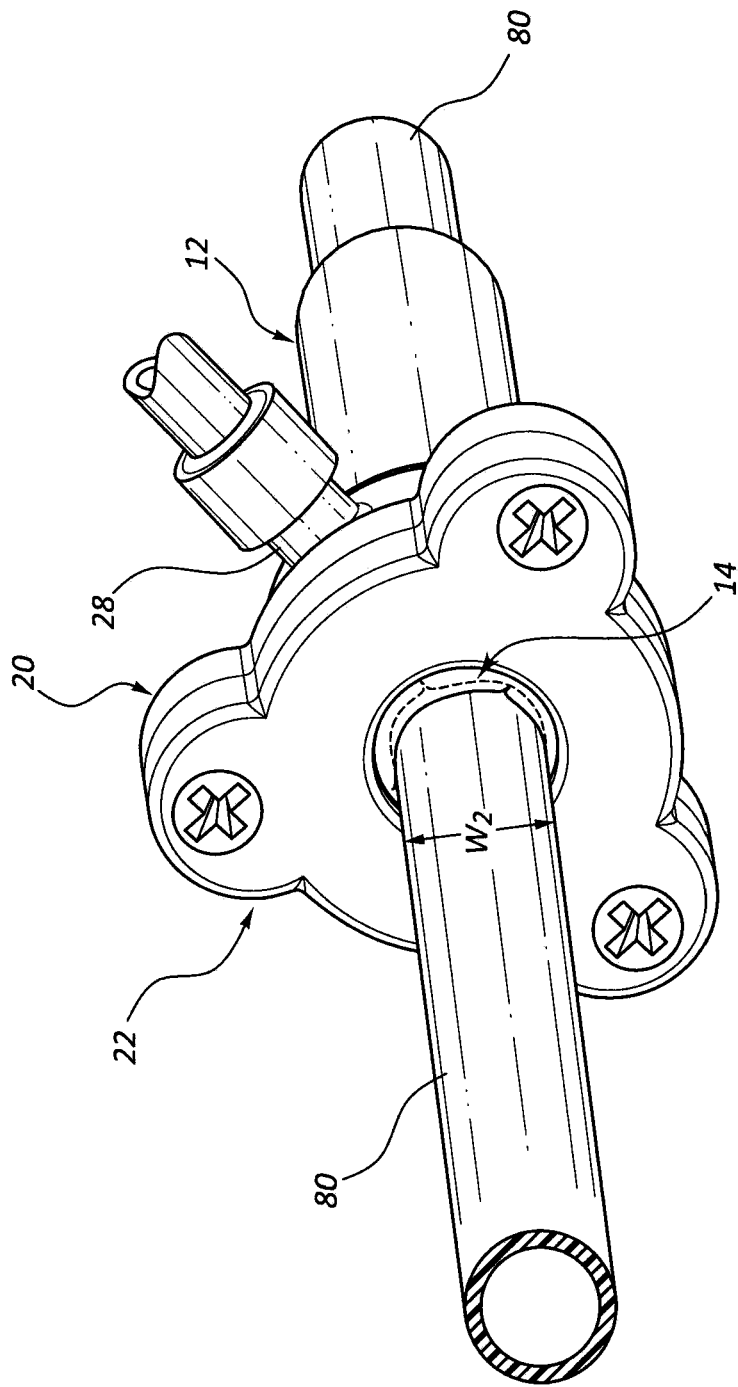
FIG. 12 is a perspective view of the introducer of FIG. 1 with a dilator inserted therein.

Referring now to FIG. 12, a dilator 80 is shown inserted through the introducer for positioning within a vessel puncture. The dilator 80 has a width $W_2$ that is less than the width $W_1$ of the seal member 14. FIG. 12 shows the seal interface between the seal member 14 and dilator 80. Inserting the dilator 80 through seal member 14 ruptures the slit interface 58 to connect the first and second slits 54, 56. Surfaces of the first and second slits 54, 56 along the first and second slit depths $D_1$, $D_2$ contact the outer surface of the dilator 80 to enhance the seal interface therebetween.

Figure 13:
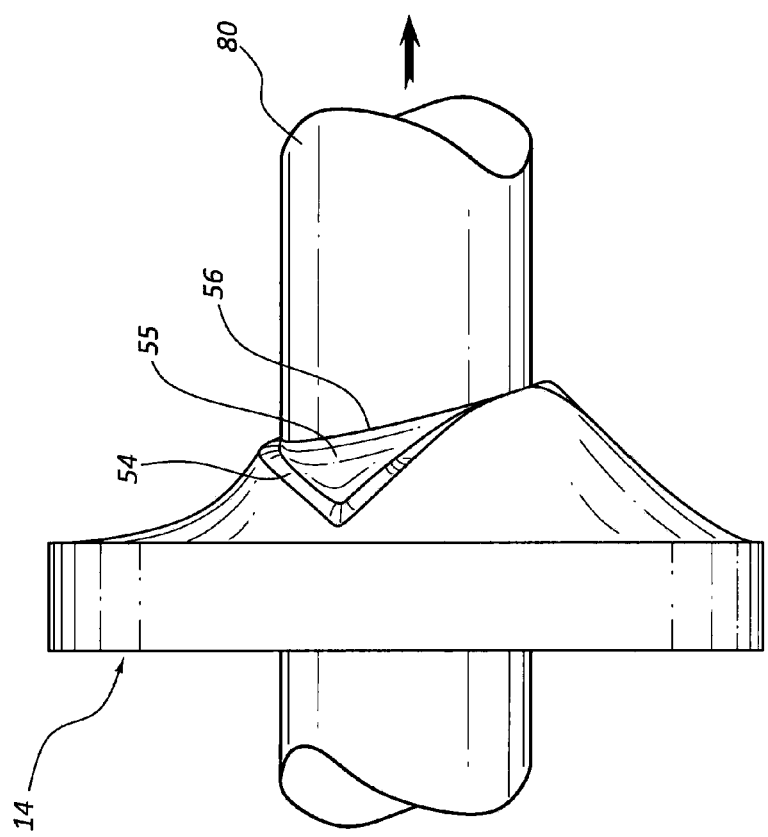
FIG. 13 is a side view of the dilator and sealing member show in FIG. 12.

The first and second slits 54, 56 may form flaps 55 of material (see FIG. 13) that seal along the outer surface of the dilator 80 or any other object that is inserted through the seal member 14. The flaps 55 may help seal gaps 155, 255 that otherwise exist around a dilator 80 that extends through slits 154 and 254, 256 in prior art seal members 114, 214, respectively, as shown in FIGS. 16A-16B and 17A-17B.

Figure 14:
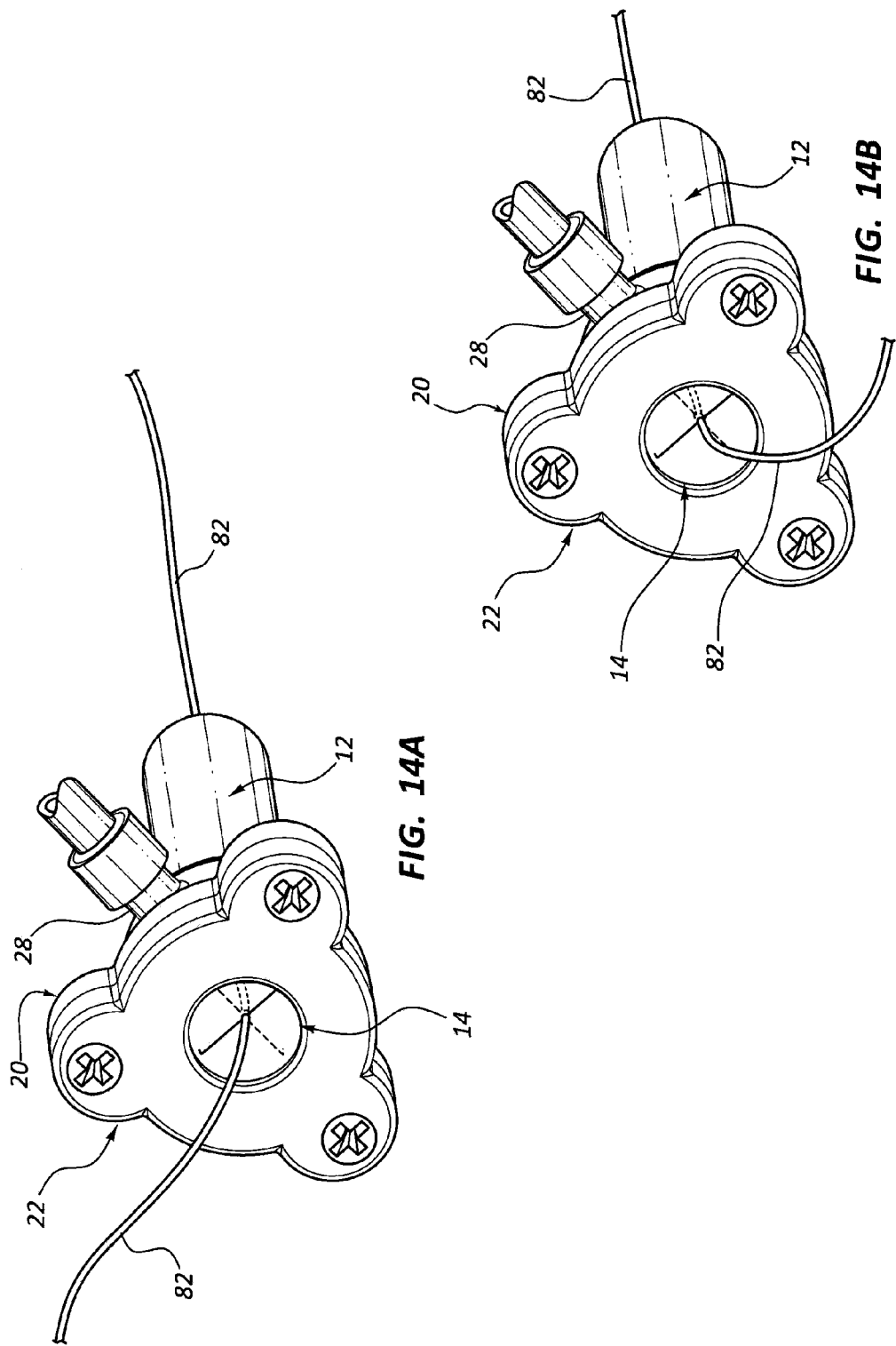
FIG. 14A shows the introducer of FIG. 1 with a guidewire extending through the sealing member in a first position.
FIG. 14B shows the introducer and guidewire of FIG. 14A with the guidewire in a second position.

FIGS. 14A and 14B show a first guidewire 82 extending through the seal member 14. The first guidewire 82 may be adjusted into various angled positions as shown in FIGS. 14A and 14B and a seal is still maintained with the seal member 14. Typically, the first guidewire 82 is positioned extending through the slit interface 58 so that portions of the seal member 14 that define the first and second slits 54, 56 and the flaps 55 contact the first guidewire 82.

Figure 15:
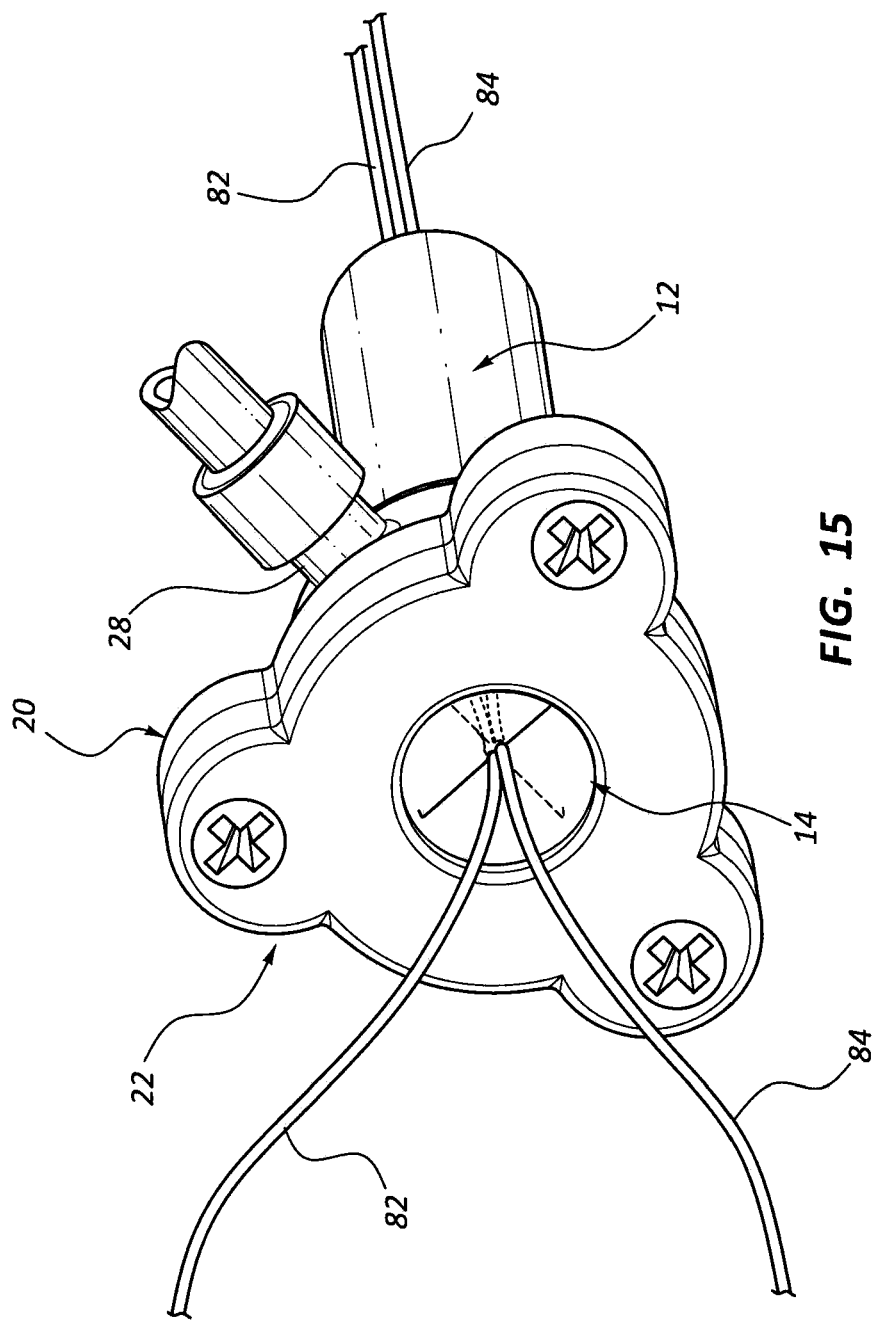
FIG. 15 shows the introducer of FIG. 1 with a pair of guidewires extending through the sealing member.
Figure 16B:
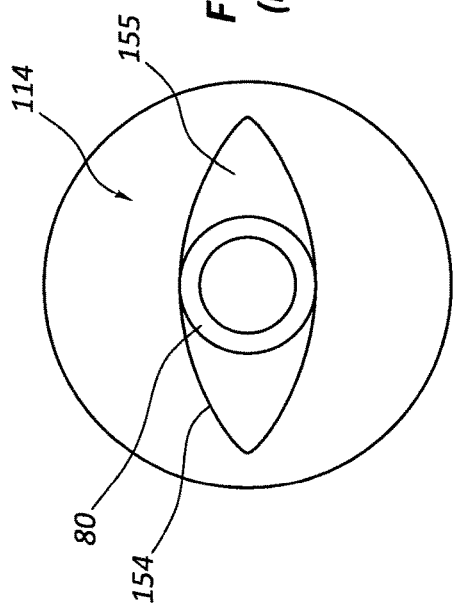
FIGS. 16A and 16B show a sealing member according to the prior art.
Figure 17B:
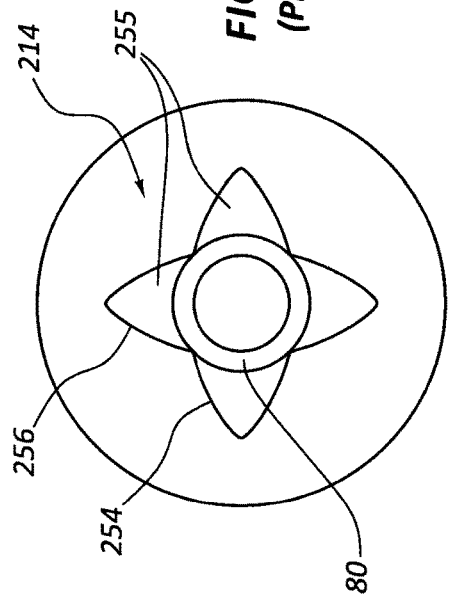
FIGS. 17A and 17B show another sealing member according to the prior art.
Figure 16A:
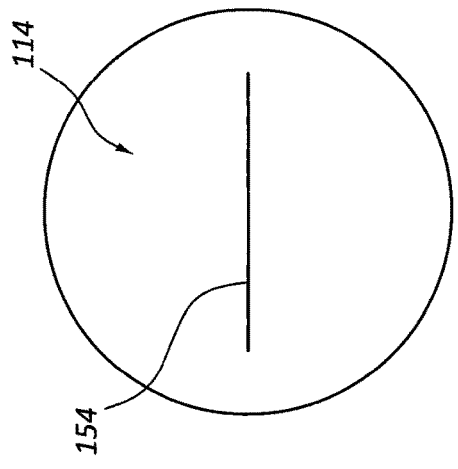
Figure 17A:
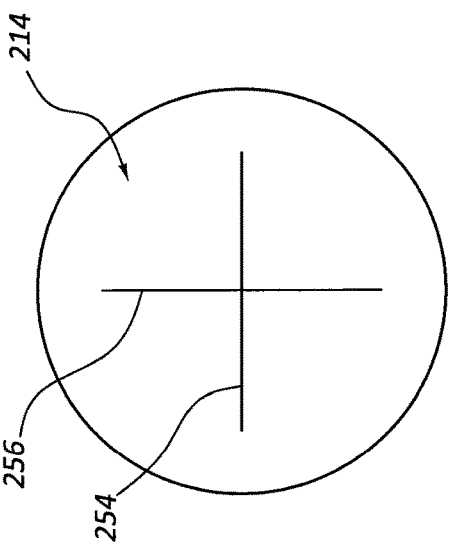

FIG. 15 shows a pair of first and second guidewires 82, 84 extending through the seal member 14. The seal member 14 may provide a sealed interface with the first and second guidewires 82, 84 regardless of the angled orientation of the first and second guidewires 82, 84. The first and second guidewires 82, 84 typically both pass through the slit interface 58. Portions of the seal member 14 that define the first and second slits 54, 56 and flaps 55 contact each of the first and second guidewires 82, 84.

The orientation, size and shape of the first and second slits 54, 56 may improve a sealed interface with any instrument that is inserted through the seal member 14 regardless of the size and shape of the instrument, the combination of instruments extending through the seal member 14, and the order in which the instruments are inserted through and removed from the seal member 14. For example, the relatively large dilator 80 may be inserted through the seal member 14 to treat the patient. The dilator 80 ruptures the slit interface 58 to provide communication between the first and second slits 54, 56 along substantially an entire length $L_1$, $L_2$ of both the first and second slits 54, 56. After the dilator 80 is removed, the first and/or second guidewire 82, 84 may be inserted through the seal member 14. Even though the slit interface 58 has been ruptured and the first and second slits 54, 56 extend from the first surface 50 to the second surface 52 along substantially their entire $L_1$, $L_2$, the seal member 14 is typically able to maintain a sealed interface with the first and second guidewires 82, 84. The first and second guidewires 82, 84 may be removed and replaced with other instruments, or other instruments may be inserted along with the first and second guidewires 82, 84 and the seal member 14 may continue to maintain the sealed interface with any of those instruments extending through the seal member 14.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. An introducer, comprising:
   a housing having a hub, a cap, and a lumen;
   a flexible seal positioned across the lumen and retained between the hub and the cap, the flexible seal comprising:
   a top surface and a bottom surface;
   a bottom slit formed in the bottom surface, the bottom slit having a bottom slit length;
   a top slit formed in the top surface, the top slit having a top slit length, the top and bottom slit lengths being arranged in an overlapping criss-cross shape;
   wherein the flexible seal is biased by an interface between the hub and the cap in a manner at least partially closing the top slit, at least partially opening the bottom slit, and bowing the flexible seal in a direction defined along a longitudinal axis extending through the lumen of the housing.

2. The introducer of claim 1, wherein at least one of the bottom and top slits has a contoured shape when opened.

3. The introducer of claim 1, wherein the bottom slit is arranged perpendicular to the top slit.

4. The introducer of claim 1, wherein the top and bottom slits each have a depth less than one half of a thickness of the flexible seal.

5. The introducer of claim 1, wherein the hub comprises a protrusion that biases the flexible seal proximally.

6. The introducer of claim 1, wherein the flexible seal comprises silicone.

7. The introducer of claim 1, wherein the flexible seal includes an integral, single-piece construction.

8. The introducer of claim 1, wherein the hub and cap are positioned at a proximal end of the housing.

9. The introducer of claim 1, wherein the top slit is biased completely closed.

10. A seal member for use in an introducer, the seal member comprising:
    a first surface having a first slit, the first slit extending through a first partial thickness of the seal member, the first surface being bowed;
    a second surface opposed to the first surface and having a second slit, the second slit extending through a second partial thickness of the seal member, the second surface being bowed;
    wherein the first and second slits each have lengths that are oriented substantially perpendicular to each other and criss-crossing each other.

11. The seal member of claim 10, wherein the first and second slits overlap.

12. The seal member of claim 11, wherein a continuous portion of a thickness of the seal member extends between the first and second slits at a location where the first and second slits overlap.

13. The seal member of claim 10, wherein the first and second partial thicknesses are no greater than 50% of a thickness of the seal member.

14. The seal member of claim 10, wherein the seal member is circular shaped.

15. A method of assembling an introducer, comprising:
providing a hub, a cap, and a seal member, the seal member having first and second slits formed in opposing top and bottom surfaces thereof, the first and second slits extending through a partial thickness of the seal member, the first slit having a first slit length, the second slit having a second slit length, the first and second slit lengths overlapping and criss-crossing each other;
compressing the seal member between the hub and the cap in a manner at least partially closing the first slit, at least partially opening the second slit, and bowing the seal member in a direction perpendicular to the top and bottom surfaces.

16. The method of claim 15, wherein at least one of the hub and the cap includes a protrusion that biases the seal member proximally when compressing the seal member.

17. The method of claim 15, wherein the first and second slits extend through no more than one half of a thickness of the seal member.

18. The method of claim 15, wherein the introducer includes a lumen, and the seal member extends across the lumen to seal the lumen.

19. A method of accessing a body cavity, comprising:
providing an introducer, a guidewire, and a dilator, the introducer having a lumen and a seal member extending across the lumen, the seal member having a first slit formed in a first surface thereof and a second slit formed in a second surface thereof, the first and second surfaces being bowed, the first and second slits each extending through a partial thickness of the seal member, the first and second slits overlapping and criss-crossing each other to form a slit interface, wherein the seal member is compressed in a direction perpendicular to the first and second surfaces;
inserting the introducer through a tissue puncture and into the body cavity;
inserting one of the guidewire and the dilator through the lumen and the first and second slits of the seal member and into the body cavity, the seal member providing a seal around a peripheral surface of the guidewire or dilator.

20. The method of claim 19, wherein inserting the guidewire or dilator tears through the seal member to pass from the first slit to the second slit.

21. The method of claim 19, wherein the introducer comprises a hub and a cap, the seal member being compressed between the hub and cap to at least partially close the first slit and at least partially open the second slit.

22. An introducer, comprising:
a housing having a hub, a cap, and a lumen;
a flexible seal positioned across the lumen and retained between the hub and the cap, the flexible seal comprising:
a top surface and a bottom surface;
a bottom slit formed in the bottom surface;
a top slit formed in the top surface, the top and bottom slits being arranged in an overlapping criss-cross shape;
wherein the flexible seal is biased by an interface between the hub and the cap in a manner at least partially closing the top slit, at least partially opening the bottom slit, and bowing the flexible seal in a direction defined along a longitudinal axis extending through the lumen of the housing, wherein the hub comprises a protrusion that proximally biases the flexible seal.

23. A method of assembling an introducer, comprising:
providing a hub, a cap, and a seal member, the seal member having first and second slits formed in opposing top and bottom surfaces thereof, the first and second slits extending through a partial thickness of the seal member, the first and second slits overlapping and criss-crossing each other;
compressing the seal member between the hub and the cap in a manner at least partially closing the first slit, at least partially opening the second slit, and bowing the seal member in a direction perpendicular to the top and bottom surfaces, wherein at least one of the hub and the cap includes a protrusion that proximally biases the seal member when compressing the seal member.

* * * * *